United States Patent [19]

Bencsits

[11] Patent Number: 5,641,499

[45] Date of Patent: Jun. 24, 1997

[54] INSECTICIDAL PRODUCT

[75] Inventor: Franz Bencsits, Wehrenbachhalde 54, 8053 Zürich, Switzerland

[73] Assignees: Franz Bencsits; Perycut-Chemie AG, both of Zurich, Switzerland

[21] Appl. No.: 988,924

[22] PCT Filed: Sep. 12, 1991

[86] PCT No.: PCT/EP91/01736

§ 371 Date: May 4, 1993

§ 102(e) Date: May 4, 1993

[87] PCT Pub. No.: WO92/03927

PCT Pub. Date: Mar. 19, 1992

[30] Foreign Application Priority Data

Sep. 12, 1990 [DE] Germany ............................ 9012996 U

[51] Int. Cl.$^6$ ...................................................... A01N 25/34
[52] U.S. Cl. ........................... 424/411; 424/403; 424/413; 424/416
[58] Field of Search ................................ 424/403, 405, 424/413, 411, 416

[56] References Cited

U.S. PATENT DOCUMENTS

| | | |
|---|---|---|
| 2,375,250 | 5/1945 | Riemenschneider et al. . |
| 2,383,815 | 8/1945 | Riemenschneider et al. . |
| 2,485,640 | 10/1949 | Vahlteich et al. ............... 99/163 |
| 3,560,613 | 2/1971 | Miskus et al. . |
| 4,668,666 | 5/1987 | Allan et al. ...................... 514/63 |
| 4,674,445 | 6/1987 | Cannelongo ..................... 119/156 |
| 4,683,132 | 7/1987 | Ronning et al. ................. 424/409 |
| 4,923,745 | 5/1990 | Wolfert et al. .................. 428/35.4 |
| 5,102,662 | 4/1992 | Gallagher ........................ 424/409 |
| 5,334,585 | 8/1994 | Derian et al. .................... 514/74 |

FOREIGN PATENT DOCUMENTS

| | | |
|---|---|---|
| 625683 | 7/1949 | United Kingdom . |
| 2 002 635 | 2/1979 | United Kingdom . |
| WO84/00095 | 1/1984 | WIPO . |
| WO85/03197 | 8/1985 | WIPO . |

OTHER PUBLICATIONS

Food Science and Technology Abstracts (FSTA) 85:973; Abstracting, Kanematsu et al., "Studies on the improvement of antioxidant effect of tocopherols . . ." Yukagaku, vol. 32 (12), 1983, pp. 731–734.

J. Agri. Food Chem., vol. 30, No. 2 (1972) pp. 313–315, "Stabilization of Thin Films of Pyrethrins and Allethrin", Miskus et al.

JP, A, 59 065 001, Patent Abstracts of Japan, 8(162):(C–236) [1599] 1984.

JP, A, 60 064,902, Patent Abstracts of Japan, 9(196):(C–297) [1919] 1985.

JP, A, 62 283 901, Patent Abstracts of Japan, 12(176):(C–498) [3023] 1988.

Primary Examiner—Neil S. Levy
Attorney, Agent, or Firm—Finnegan, Henderson, Farabow, Garrett & Dunner, L.L.P.

[57] ABSTRACT

The invention relates to an insecticidal product which comprises a vehicle impregnated with an insecticidal composition. The insecticidal composition contains at least one pyrethroid, at least one UV absorbing agent and at least one antioxidant from the group consisting of tocopherol derivatives, ascorbyl palmitate and citric acid esters and is preferably applied onto a polyethylene sheet as an emulsion. The product is used as a "carpet" for controlling flying and crawling insects such as flies and cockroaches.

5 Claims, No Drawings

INSECTICIDAL PRODUCT

The present invention relates to an insecticidal product comprising a support impregnated with an insecticidal composition, the insecticidal composition containing in each case 0.001 to 10% by weight of at least one pyrethroid, at least one UV absorbing agent and at least one anti-oxidant, and its use for controlling flying and crawling insects.

The insecticidally effective components of pyrethrum and its synthetic analogues, which are derived from the structure indicated in the following, are designated as pyrethroids. The main active substances in pyrethrum are the cinerins I and II, the pyrethrins I and II and the jasmolins I and II (Römpps Chemie-Lexikon, 8th edition (1987), page 3413).

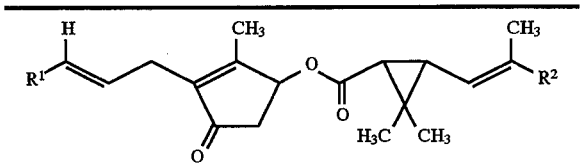

| | |
|---|---|
| Pyrethrin I: | $R^1 = CH=CH_2$, $R^2 = CH_3$ |
| Pyrethrin II: | $R^1 = CH=CH_2$, $R^2 = COOCH_3$ |
| Cinerin I: | $R^1 = R^2 = CH_3$ |
| Cinerin II: | $R^1 = CH_3$, $R^2 = COOCH_3$ |
| Jasmolin I: | $R^1 = C_2H_5$, $R^2 = CH_3$ |
| Jasmolin II: | $R^1 = C_2H_5$, $R^2 = COOCH_3$ |
| Allethrin: | $R^1 = H$, $R^2 = CH_3$ |

Pyrethrum is obtained from the dried flower heads of various pyrethrum or chrysanthemum species by pulverization or extraction and contains as main active substances pyrethroids such as pyrethrins, cinerins and jasmolins. Apart from nicotine, pyrethrum is the strongest vegetable insecticide; however, its effectiveness is reduced by sunlight and heat (Römpps Chemie-Lexikon, 8th edition (1987), page 3414). The lack of stability, but also the high price of natural pyrethroids led to the development of numerous synthetic derivatives.

Pyrethroids are generally used as isomer mixtures. They have been used for a long time as insecticides, in particular against common houseflies, cockroaches or blackbeetles and other household vermin, moths, corn weevils, mosquitoes, garden and greenhouse parasites, hay worms in viticulture and boll-weevils. Particularly the natural pyrethroids distinguish themselves by a rapid so-called knock-down effect, i.e. the insects are certainly paralyzed rapidly, but only temporarily, and they recover again. The oxidative detoxication metabolism of the insects is responsible for this undesired effect.

Due to the instability of pyrethroids to light and air oxygen, UV stabilizers and antioxidants are added, as a rule, to the pyrethroid insecticides. GB-A-2 002 635 describes a rapidly evaporating, pyrethroid insecticide, which contains, in addition to a pyrethroid, at least one compound from the group consisting of phthalic acid esters, aliphatic esters, aliphatic, dibasic esters, aromatic carboxylic acid esters, higher aliphatic alcohols, alcohols with several OH groups, glycol esters and hydrocarbons with 10 or more carbon atoms and an antioxidant. Dibutyl hydroxy toluene, butyl hydroxy anisole, n-propyl gallate, tocopherol, octadecyl-3-(3,5-di-tert.-butyl-4-hydroxy phenyl) propionate, pentaerythitol tetrakis-[3-(3,5-di-tert.-butyl-4-hydroxy phenyl) propionate], 2,5-di-tert.-butyl hydroquinone, 4,4'-thiobis-(3-methyl-6-tert.-butyl phenol) and 2,2'-methylene-bis-(4-methyl-6-tert.-butyl phenol) are mentioned. This pyrethroid insecticide can also be applied onto a porous carrier or be present in the form of a paste, a cream or granules, and it is heated to 150° to 400° C. by a separate heating element in order to evaporate it rapidly.

U.S. Pat. No. 3,560,613 describes an insecticidal composition of a pyrethroid, an UV absorbing agent and a long-term antioxidant. The antioxidant is either 2,6-di-tert.-butyl-4-methyl phenol or 2,6-dioctadecyl paracresol.

Insecticidal, pyrethroid-containing compositions against crawling and flying insects are customarily sprayed onto the area to be treated by means of pressurized packages or hand pumps or are put out in powder form as baits. These application forms have the disadvantage that the insecticidal composition is removed when the treated area is cleaned and must consequently be applied again to maintain the desired effectiveness, which results in a high consumption of insecticide and thus high costs during long-term application.

For the control of annoying insects and parasites in mammals, such as stable flies, horn flies, ticks and mites, collars made of porous material, which are soaked with a pyrethroid composition and covered with a membrane, can e.g. be put on the animals. This composition can contain UV absorbing agents and antioxidants as additives (WO 85/03197). DE-A-3 421 290 describes a pest control sheet made of a carrier material impregnated with a pest control agent and a cover for this carrier material which is made of Japanese paper, nonwoven fabric, fabric or paper, through which the pest control agent can evaporate in controlled fashion. Papers and nonwoven fabrics are in particular indicated as carrier materials. The pest control agent is not specified in greater detail. The described, insecticide-containing materials slowly release the insecticide to the environment. However, they are not suited to be used against crawling insects, e.g. in households, since, on the one hand, they are too thick and, on the other, they are too sensitive due to their layer structure of porous material and membrane.

Therefore it is the object of the present invention to provide an improved insecticidal product, which can also be well used against crawling insects, is insensitive to damage and whose effectiveness can be utilized for a long period of time.

This object is solved by an insecticidal product of the indicated type, which is characterized in that the contained antioxidant is a citric acid ester.

The insecticidal product according to the invention is especially suited for exterminating vermin such as household vermin, in particular flies and cockroaches or blackbeetles.

As compared with the conventional, pyrethroid-containing compositions, the product according to the invention has the great advantage that it is "mobile", i.e. it can be easily removed during each cleaning of the treated surface, and after cleaning, it can be brought again into position. Consequently, the product according to the invention is also designated as a "carpet" in the following.

Due to the mobile application of the product according to the invention, the effectiveness of the insecticidal composition can be fully utilized so that a lasting pest control is ensured with a small amount of insecticide.

Moreover, the product according to the invention is ecologically very beneficial and can be disposed of in simple fashion.

The support used according to the invention may consist of each customary, impregnatable material which can be of a natural or synthetic nature and includes fabrics and non-woven fabrics and it may also consist of metallic materials. For cost reasons, a foam material is preferred, in particular one made of polyethylene.

In a further preferred embodiment, the support consists of a polyethylene sheet, in particular with a thickness of 0.0001 to 0.49 mm, which is not perceived as an obstacle by crawling insects. A penetration of the insecticide through the support to its lower side is prevented by the polyethylene sheet, whereby the full effectiveness is ensured.

The support is preferably applied onto an antiskid carrier such as rubber or plastics. For environmental reasons, paper, such as cardboard, is also preferred. The connection of the support with the carrier can be carried out in every customary fashion, a laminating being preferred.

After a reduction in the effectiveness of the insecticidal composition, the product according to the invention can e.g. be rolled up like a carpet for disposal. It has preferably carrying handles so that it can be folded together like a bag.

For the easy and non-detrimental disposal of the product according to the invention the surface of the carrier is preferably larger than the surface of the support so that the carrier projects beyond the support on both sides, and the user does not get into contact with the impregnated surface.

If the insecticidal effectiveness decreases, the product according to the invention can also be impregnated again with the insecticidal composition.

All natural and synthetic pyrethroids, either alone or in mixture, can be used in the insecticidal composition used according to the invention. Natural pyrethrum proved to be especially effective.

The pyrethroid is preferably used in an amount of 0.001 to 10% by weight, especially preferred of 0.01 to 2% by weight, in particular of 0.03% by weight, based on the composition.

To improve the stability of the insecticidal composition used according to the invention with respect to air and light, it contains at least one UV asorbing agent and at least one antioxidant. The insecticidal effectiveness of the product according to the invention is drastically prolonged by the selection of the antioxidant from citric acid esters.

The insecticidal composition can contain a tocopherol derivative and/or ascorbyl palmitate as a further antioxidant.

The tocopherols or derivatives thereof are preferred as further antioxidant. Tocopherols are natural substances with vitamin E character and are consequently often also designated as vitamin E. They are derived from the basic structure tocol and differ in the degree of methylation at its benzene nucleus. All known tocopherols can be used according to the invention. The DL-$\alpha$-, -$\beta$-, -$\gamma$- and -$\delta$- tocopherols are preferred. Tocopherols are in particular used as a mixture in a suited ratio with one citric acid ester and, possibly, ascorbyl palmitate.

The citric acid esters are preferably mono- to triesters of citric acid with alkyl alcohols having 1 to 8 carbon atoms.

UV absorbing agents used according to the invention are generally known. Especially suited UV absorbing agents, which are effective in the wave length range of 250 to 350 nm, which is of interest here, are benzoic acid derivatives, e.g. p-amino benzoic acid derivatives such as amyl-p-dimethyl amino benzoate and glyceryl-p-amino benzoate or o-hydroxy benzoic acid derivatives; benzophenone derivatives, e.g. 2-hydroxy-4-(2-hydroxy-3-methacryloxy) propoxy benzophenone or 2-hydroxy-4-methoxy benzophenone-5-sulfonic acid; camphor derivatives, coumarin derivatives, benzimidazole derivatives; dibenzoyl methane derivatives; cinnamic acid ester methane salts of a sulfonic acid such as tris-(hydroxy methyl) aminomethane salt of 2-phenyl benzimidazole-5-sulfonic acid.

The UV absorbing agent is preferably used in an amount of 0.001 to 10% by weight, especially preferred of 0.01 to 5% by weight, in particular of 0.03% by weight, based on the composition.

The antioxidant is used in the composition used according to the invention preferably in an amount of 0.001 to 10% by weight, especially preferred of 0.01 to 5% by weight, in particular of 0.03% by weight, based on the composition.

The insecticidal composition used according to the invention is suitably produced in liquid form with the addition of a diluent or solvent. Suited diluents are water, organic solvents or oils, an aqueous and/or oily emulsion being preferred. Monohydric and polyhydric alcohols, glycols such as 1,2-propane diol, esters or fatty acids, can e.g. be used as organic diluents, while mineral oils, saturated and unsaturated ceric acid esters and fatty acid esters, e.g. vegetable oils and natural and synthetic ethereal oils are especially well suited as oils. In addition, the insecticidal composition may contain lecithin. The insecticidal composition is then sprayed onto the support used according to the invention.

The insecticidal product according to the invention can be used against any type of vermin, against which the already known pyrethroid compositions are used. It has an excellent long-term effect against flying insects such as common houseflies aand moths, and crawling insects such as cockroaches, ants, silverfish, isopods and beetles.

To test the insect-attracting and insecticidal effectivenesss, products according to the invention were used as a "carpet" with flying and crawling insects. The products are produced by impregnating a 5 mm thick polyethylene foam support with an insecticidal composition containing 0.3% by weight of pyrethrum, 0.15 by weight of tocopherol acetate, 0.1% by weight of tris-(hydroxy methyl) aminomethane salt of 2-phenyl benzimidazole-5-sulfonic acid, 80% by weight of fatty alcohol polyglycol ether and 19.5% by weight of propylene glycol.

Crawling insections a) Method:

The carpets were spread in a suited test room (surface area approx. 2 m$^2$), and about 30 blackbeetles were released in this room as test animals.

The percentage surface share of the carpet, based on the surface area of the test room, was 10%. Test animals with definitive damage (dorsal position for blackbeetles) were counted and indicated in percent.

The test was repeated after a one-, two-, three and four-months storage of the carpets at room temperature and normal average illumination conditions.

b) Results:

Insect-attracting effect:

The carpet had a good insect-attracting effect on the test animals.

Insecticidal effect:

The shares of dead animals are represented in % according to the listed recording periods and the indicated storage times of the carpet in the indication of the results.

| Challenge times | Dead blackbeetles in % after storage times in months | | | | |
| --- | --- | --- | --- | --- | --- |
| (min) | 0 | 1 | 2 | 3 | 4 |
| 20 | 2 | 2 | 2 | 2 | 2 |
| 40 | 28 | 27 | 27 | 26 | 24 |
| 60 | 60 | 58 | 57 | 55 | 52 |
| 80 | 77 | 74 | 72 | 69 | 67 |
| 120 | 100 | 100 | 100 | 98 | 94 |

Flying insects:

a) Method:

The Peet-Grady test according to "The Peet Grady Method Official of the Chemical Specialities Manufacturers Assoc., Blue Book 1952" was modified as experimental set-up for ascertaining the effectiveness against flies.

Approximately 50 freshly hatched common houseflies (musca domestica) each served as experimental animals for each test. The experimental animals were placed in a cubic room with an edge length of 2 m (8 m$^3$ cubic content) and subjected to the effect of the spread carpet. The amounts of insecticide correspond to the conditions in the test against crawling insects (blackbeetles).

The insects which were no longer able to fly were counted after 5, 10, 15 and 20 minutes. The test room was ventilated after 15 minutes, the test animals were collected and placed into an air-permeable container in order to find out whether the damaging effect was irreversible after 24 hours.

The floor of the chamber was provided with a new plastic sheet after each test.

b) Results:

Insect-attracting effect:

Here, as well, there is a good insect-attracting effect. The insecticide can only be effective by contact with the test insects.

Insecticidal effect:

The mean values of the results can be gathered from the following table. The percentage of flight-incapacitated insects is indicated, which corresponds to the knockdown rate.

| Challenge times (min) | Dead flies in % after storage times in months | | | | |
|---|---|---|---|---|---|
| | 0 | 1 | 2 | 3 | 4 |
| 5 | 8 | 8 | 7 | 7 | 6 |
| 10 | 25 | 25 | 23 | 22 | 20 |
| 15 | 75 | 75 | 73 | 71 | 65 |
| 20 | 100 | 100 | 99 | 99 | 97 |

It can be learnt from the aforementioned results that the insecticidal product according to the invention has a sufficiently good long-term effect against flying and crawling animals.

I claim:

1. An insecticidal product comprising a polyethylene sheet laminated to a paper carrier and impregnated with a liquid insecticidal composition consisting essentially of (a) 0.001 to 10 wt. % of pyrethrum, (b) 0.001 to 5 wt. % of a tris (hydroxy methyl) aminomethane salt of a 5-sulfonic acid UV absorbing agent, (c) 0.001 to 10 wt. % of an antioxidant consisting essentially of a mono-, di-, or tri-ester of citric acid and an alkyl alcohol having from 1 to 8 carbon atoms, or a combination thereof with ascorbyl palmitate, and (d) an organic diluent selected from the group consisting of polyhydric alcohols, fatty polyglycol ethers and mixtures thereof, said insecticidal product being effective over a long term for controlling flying or crawling insects.

2. The product according to claim 1, wherein said antioxidant further consists essentially of one or more tocopherols selected from the group consisting of DL -α-,-β-, -γ-, and -δ- tocopherols.

3. A product according to claim 1, wherein the polyethylene sheet has a thickness of 0.0001 to 0.49 mm.

4. A product according to claim 1, wherein it has carrying handles on the sides.

5. A product according to claim 1, wherein the insecticidal composition contains additionally lecithin.

* * * * *